United States Patent [19]

Rait

[11] 4,332,560
[45] Jun. 1, 1982

[54] PARTICLE COLLECTOR FOR USE WITH DENTAL SUCTION APPARATUS

[76] Inventor: Joseph M. Rait, 1100 Amherst St., Buffalo, N.Y. 14216

[21] Appl. No.: 128,631

[22] Filed: Mar. 10, 1980

[51] Int. Cl.³ .............................................. A61C 17/04
[52] U.S. Cl. ..................................... 433/92; 128/276; 433/95
[58] Field of Search ............................ 433/95, 92, 91; 128/277, 278, 276; 137/800

[56] References Cited

U.S. PATENT DOCUMENTS

| | | | |
|---|---|---|---|
| 1,202,971 | 10/1916 | Daiber | 433/185 |
| 3,499,393 | 3/1970 | Bent | 433/95 |
| 3,516,160 | 6/1970 | Leffler | 433/95 |
| 3,648,698 | 3/1972 | Doherty | 128/276 |
| 3,855,997 | 12/1974 | Sauer | 128/276 |

FOREIGN PATENT DOCUMENTS

| | | | |
|---|---|---|---|
| 15097 | 11/1933 | Australia | 433/95 |
| 1019560 | 2/1966 | United Kingdom | 128/276 |

*Primary Examiner*—Gene Mancene
*Assistant Examiner*—John J. Wilson
*Attorney, Agent, or Firm*—E. Herbert Liss

[57] ABSTRACT

A selectively usable particle collector for recovering precious metals in clean condition during use of dental suction apparatus is shown. A reservoir where particles are deposited has a closure cap with ports to one of which can be removably attached a replaceable pick up tube to be inserted in the patient's mouth; the other is adapted to removably receive a flexible hose leading to a vacuum source both ports being in communication with the reservoir. In another embodiment a portion of the cap can be rotated to selectively effect either direct communication from the pick up tube to the flexible hose or through the reservoir. A metering vent is provided to regulate vacuum pressure.

3 Claims, 6 Drawing Figures

U.S. Patent  Jun. 1, 1982  4,332,560
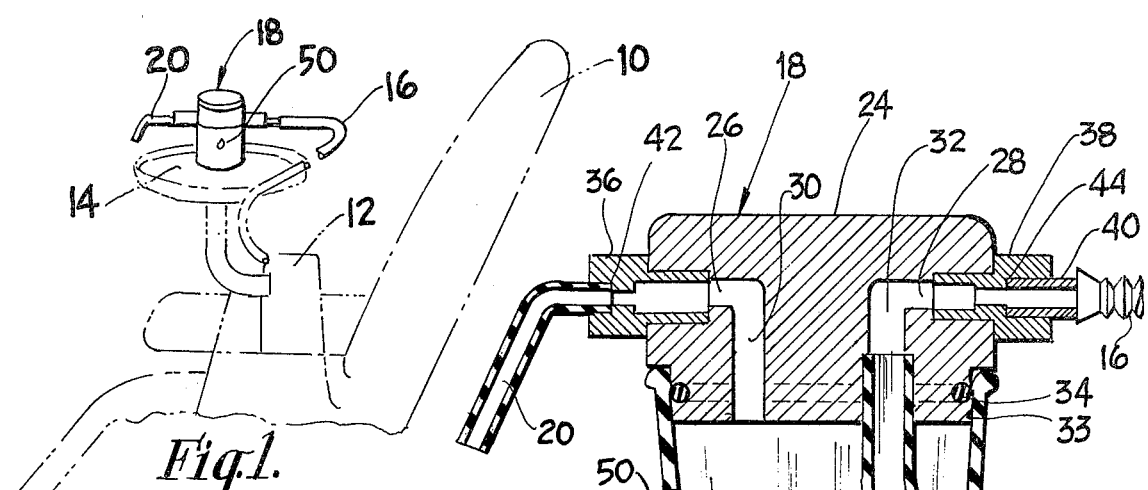
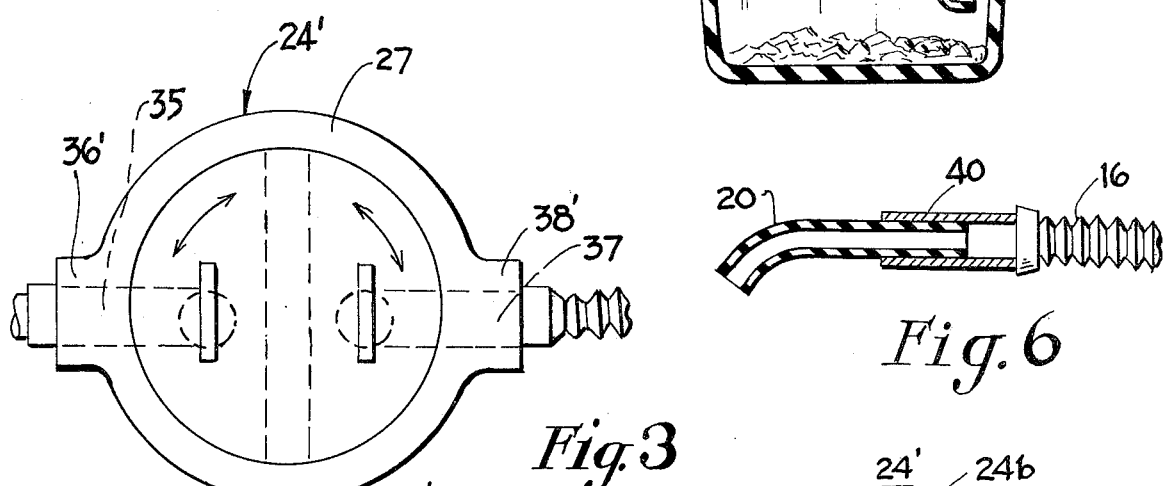
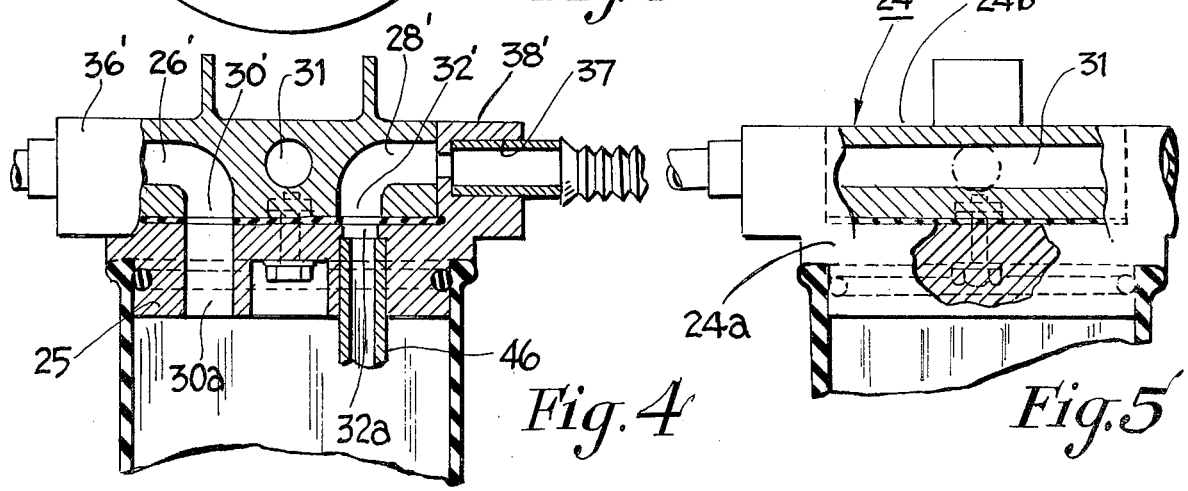

PARTICLE COLLECTOR FOR USE WITH DENTAL SUCTION APPARATUS

BACKGROUND OF THE INVENTION

The present invention relates to dental suction apparatus for cleaning debris from the mouth during a dental procedure and more particularly to a particle collector for recovering precious metals.

During dental procedure it is necessary to remove debris which collects in the patient's mouth. Suction apparatus is used for this purpose. Silver constitutes a substantial portion of this debris and it is desirable to recover as much of this precious metal as possible in a relatively clean condition. It is known in the dental art to recover amalgam and heavier metal particles by a reservoir or trap connected in the suction line of an aspirator as shown in U.S. Patent to Ritchie, U.S. Pat. No. 3,777,403 issued Dec. 11, 1973. However, the known devices are designed to remain in service continuously during a dental procedure or for a longer period of time. The U.S. Patent to Wiley, U.S. Pat. No. 4,088,706, discloses a filter trap which is adapted to be readily removed and inserted. The Wiley patent utilizes a filter element to define the collection chamber and thus is limited in capacity to the capacity of the filter.

In the course of a dental procedure the aspirator is utilized to remove a mixture of tartar scraped from the teeth, tooth particles, bone, ground off tooth swarf, blood, blood clots, particles of cotton, saliva and other debris. A trap such as that shown in U.S. Pat. No. 3,777,403 remains operative continuously and collects all of such debris. The largest portion of the excess silver amalgam can be recovered during the final stages of the filling procedure when the dentist has completed inserting the amalgam into a prepared cavity and is trimming the filling to produce a good anatomical shape. The cavity is overfilled to provide excess material so that the filling can be trimmed to a proper shape. During this stage the mouth is relatively clean of all debris except for saliva and amalgam. Thus if the amalgam collector can be limited to operation only during the above mentioned trimming operation, a relatively clean collection of amalgam and some saliva can be retained. This collection is more readily acceptable to silver refiners than is the amalgam mixed with bone, blood, particles of cotton and other debris.

SUMMARY OF THE INVENTION

The collector of the present invention includes a transparent reservoir and a removable closure cap. The closure cap is preferably of metal which can be sterilized and the reservoir is of plastic and is disposable. Inlet and outlet ports are provided in the cap in fluid communication with the reservoir. The ports are preferably formed internally of the cap structure.

The suction apparatus includes a flexible conduit connected at one end to a vacuum source. A fixture is provided at the other end of the flexible conduit and is adapted to receive, internally, a readily removable and replaceable pick up tube, preferably disposable, which is, during use, inserted in the patient's mouth to collect debris. A nipple corresponding internally to the fixture is secure to the inlet port of the particle collector. The outlet port is provided with a nipple, dimensioned to receive the fixture internally in a readily removable and replaceable manner. Thus it should be apparent that the dentist or his aide can rapidly and without significant interruption of the procedure selectively insert the collector into the evacuation system at the desirable stage in the procedure when the debris is in a relatively clean condition. At least one metering opening is provided either in a nipple or in the reservoir to regulate vacuum pressure. Because the collector is positioned at the working position, the dentist or his aide can manually cover or partially cover the opening, if necessary, depending on the value of vacuum pressure required. This requlation means enables the operator to adjust the vacuum pressure to prevent aspiration of the collected particles from the reservoir, to assure adequate pressure for clean up of the particles from the patient's mouth and at the same time to maintain the vacuum pressure at a level which will not cause discomfort to the patient. This is possible because the operator can observe both the patient and the reservoir while the apparatus is in use.

In another embodiment of the invention a modified closure cap is employed in which the inlet and outlet ports extend radially on the same diametrical axis of a disc shaped element. On a second diametrical axis a bore extends through the disc shaped element connecting the inlet and outlet ports.

The disc shaped element is rotatably mounted concentrically within a ring. The nipples extend radially outward from the ring from opposite ends of a diametrical axis. The cap can be rotated to align the inlet and outlet ports with the nipples or alternatively the straight through bore can be aligned with the nipples. In the latter position of the disc element the pick up nozzle is connected directly to the flexible tubing leading to the vacuum source through the straightthrough bore thereby by-passing the reservoir. The disc element can also be rotated to an intermediate position closing off the vacuum source entirely.

It is therefore an object of the invention to provide a simple, economical particle collector for use with dental suction apparatus which is readily accessible to the dentist or his aide during a dental procedure and which is selectively operable and readily controllable without significant interruption of a dental procedure.

Another object of the invention is to provide a simple, economical particle collector for dental suction apparatus which can be readily inserted and removed for selective use so as to collect only relatively clean particles of precious metals.

A further object of the invention is to provide a particle collector which includes readily accessible vacuum adjustment capability without interruption of the dental procedure to provide adequate vacuum pressure to remove debris from the patient's mouth and yet avoid patient discomfort and aspiration of the collected particles from the collector reservoir.

Other objects and advantages of the invention will be apparent from the following detailed description taken in connection with the accompanying drawings.

BRIEF DESCRIPTION OF THE DRAWINGS

FIG. 1 is a perspective view of a dental chair illustrating the particle collector of the invention operatively connected to the suction apparatus;

FIG. 2 is a sectional view of the preferred embodiment of the particle collector;

FIG. 3 is a top elevational view illustrating a modified embodiment of the invention;

FIG. 4 is a fragmentary sectional view illustrating the embodiment of FIG. 3 adjusted for particle collection;

FIG. 5 is a fragmentary view partly in section illustrating the embodiment of FIGS. 3 and 4 adjusted to by-pass the collector reservoir; and FIG. 6 is a fragmentary view illustrating the suction apparatus with the collector removed.

In FIG. 1 there is shown a dental chair 10 and a console 12 adjacent thereto. A table 14 for placement of instruments and supplies accessible to the dentist is affixed to the console 12. A flexible conduit 16 is connected at one end to a vacuum source and sump (not shown) within the console 12 and extends to the table 14. At its other end the conduit 16 is attached to a particle collector 18. A removable and replaceable pick up tube 20 is connected to the particle collector 18.

Referring particularly to FIG. 2, a particle collector 18 is illustrated which comprises a transparent plastic, open ended, cylindrical reservoir 22 closed by a closure cap 24 of stainless steel, aluminum or other suitable material capable of sterilization. Inlet and outlet ports 26 and 28 extend radially from a side wall preferably on a common diametrical axis and terminate in angularly disposed ducts 30 and 32 opening at the underside of the cap 24. Adjacent its underside the cap 24 is of reduced diameter as at 33 and fitted with an O-Ring 34 to engage within the open end of the reservoir 22 in sealed engagement. Nipples 36 and 38 extend radially outwardly from inlet and outlet ports 26 and 28, respectively, and may be secured in any suitable or desirable manner as for example by a sweat fit as shown or it may be formed integrally as shown in FIG. 3. The disposable plastic pick up tube 20 and a metal fitting 40 telescopically engage in frictional engagement within nipples 36 and 38 respectively. The nipples 36 and 38 include internal circumferential shoulders 42 and 44, respectively, against which the pick up tube 20 and the fitting 40 abut to limit inward movement. The metal fitting 40 is provided at the free end of flexible conduit 16 and is of the same internal diameter as the nippled 38 so as to accomodate pick up tube 20.

A downspout tube 46 extending into the reservoir 22 from duct 32 may be provided to aspirate moisture within the reservoir.

As shown an elongate metering opening 50 is provided in a sidewall of the reservoir to regulate vacuum pressure. The dentist when using the suction equipment can place a thumb or finger over the opening if increased vacuum is required or he may leave the opening uncovered for reducing pressure to prevent aspiration of the collected particles or for patient comfort.

In accordance with the broader aspects of the invention the opening may be provided at any other convenient location as for example in one of the nipples; multiple openings may be provided in lieu of an elongate opening.

A modified embodiment of the invention is illustrated in FIGS. 3, 4 and 5 which does not require detachment of the particle collector 18.

In the modified embodiment the closure cap 24' includes a base 24a and a disc element 24b. The base 24a comprises a base plate 25 having an upstanding circumferential flange or ring 27 forming a cylindrical recess which accomodates the disc element 24b in close fitting relationship. The disc element 24b is rotatably secured to the base plate 25. Inlet and outlet ports 26' and 28' identical to the ports 26, 28 are provided in the disc element 24b on opposite ends of a diameter and terminate in ducts 30', 32' extending through the underside of the disc element 24b. On another diameter of the disc element, a straight through bore 31 is provided. The ring or flange 27 has openings 35 and 37 on opposite ends of a diameter to which nipples 36' and 38' identical to nipples 36 and 38 may be secured. Openings 30a and 32a are provided through the base plate 25 which align with the open ends of ducts 30' and 32' when the disc element 24b is rotated to align the ports 26' and 28' with the openings 35 and 37 in the flange 27.

The operation of the particle collector should now be apparent. During the drilling stage when blood, bone, and tooth fragments are being aspirated the collector 18 shown in FIG. 2 can be detached and stored in a ready position on the table 14. At this time the pick up tube 20 is placed in the metal fitting 40 disposed at the end of the flexible conduit 16 as illustrated in FIG. 6. During the trimming stage the pick up tube is positioned in the nipple 36 and the metal fitting 40 is positioned in the nipple 38 whereupon the aspirated relatively clean particles of amalgam will be deposited in the reservoir. The dentist or his aide at this time can appropriately regulate the vacuum pressure by manipulation of the metering opening area 50 with his thumb or fingers.

When the embodiment of FIGS. 3, 4 and 5 is employed the disc element 24 can be rotated to position the ports 26' and 28' in communication with the nipples 36' and 38' and the ducts 30' and 32' in communication with the openings 30a and 32a. During the drilling stage the disc can be rotated to place the straight through bore 33 in communication with the nipples 36 and 38 to thereby by-pass the reservoir to avoid collection of blood, tooth particles and other undesired debris. To shut off vacuum pressure, the disc element 24b can be rotated to a position where neither the straight through bore 33 or the ports 26' and 28' are in alignment with the ducts 30' and 32'.

It should now be apparent that an improved portable particle collector for collecting precious metals during dental procedures has been provided which is selectively operative and under the control of the dentist or his aide during the procedure so that it is in use only during those stages where relatively clean amalgam is being aspirated. The dentist or his aide can without interruption of the procedure control the vacuum pressure for the benefit of the patient's comfort and to assure that the collected particles are not aspirated from the collector while at the same time maintaining adequate vacuum pressure. Certain specific embodiments of the invention have been described for the purpose of illustration but it will be apparent that various modifications and other embodiments are possible within the scope of the invention. It is to be understood therefore that the invention is not limited to the specific arrangements shown but in its broadest aspects it includes all equivalent embodiments and modifications which come within the scope of the invention.

What is claimed is:

1. In a dental suction apparatus for cleaning debris and saliva from the mouth of a patient during a dental procedure which includes a vacuum source, a readily removable and replaceable pick up tube for insertion in a patient's mouth and a flexible conduit for connecting said pick up tube to said vacuum source, a fitting on said flexible conduit for retaining said pick up tube, a portable particle collector for separating and recovering waste particles of precious metals in a relatively clean condition adapted to be removably connected to the suction apparatus intermediate said pick up tube and said conduit comprising a reservoir and a removable closure cap for said reservoir; said closure cap having an inlet port and an outlet port, a first duct disposed in angular relationship to said inlet port and a second duct disposed in angular relationship to said outlet port, said first and second ducts being disposed to effect fluid communication between said reservoir and said inlet and outlet ports, respectively, a radially outward protruding nipple at said outlet port and a radially outwardly protruding nipple at said inlet port, said fitting having an outer surface engageable with said outlet port and an internal surface engageable with said pick up tube, said inlet port being also frictionally engageable with pick up tube whereby said pick up tube can be alternatively engaged with said fitting or said particle collector.

2. A particle collector according to claim 1 including a manually manipulatable vacuum pressure adjusting elongate opening venting to atmosphere.

3. In dental suction apparatus for cleaning debris and saliva from the mouth of a patient during a dental procedure which includes a vacuum source a readily removable and replaceable pick up tube for insertion in a patient's mouth and a flexible conduit for connecting said pick up tube to said vacuum source, and a fitting on said flexible conduit for retaining said pick up tube; a portable particle collector for separating and recovering waste particles of precious metals in a relatively clean condition adapted to be connected to the suction apparatus intermediate said pick up tube and said conduit comprising a reservoir and a removable closure cap for said reservoir; said closure cap comprising a base and a disc element rotatably secured to the base, said base comprising a base plate having an upstanding peripheral flange and a pair of spaced apart apertures through said flange on opposite ends of a diameter thereof, a nipple extending radially outwardly from each of said apertures, said disc element having inlet and outlet ports disposed on a common diameter and terminating in angularly disposed ducts opening through the underside of said disc element and a straight through bore on another diameter, one of said nipples having fitting means for retaining said pick up tube, the other of said nipples having engaging means for connection to said fitting, said disc element being disposed concentrically within said peripheral flange and rotatable from a first position wherein the open ends of said ports are disposed in alignment with said spaced apart apertures in said base plate to a second position wherein said straight through bore is in alignment with said apertures, whereby the particles can be deposited in the collector when the disc is rotated to said first position or the particles can by pass the collector when said disc is rotated to a second position without interruption of the operation of the suction apparatus.

* * * * *